United States Patent
Gil

(10) Patent No.: US 8,624,202 B2
(45) Date of Patent: Jan. 7, 2014

(54) PORTABLE STERILIZATION DEVICE FOR FOOTWEAR UTILIZING GERMICIDAL UV-C RADIATION

(75) Inventor: Patricia Gil, Indian Shores, FL (US)

(73) Assignee: Hepco Medical, LLC, Largo, FL (US)

( * ) Notice: Subject to any disclaimer, the term of this patent is extended or adjusted under 35 U.S.C. 154(b) by 420 days.

(21) Appl. No.: 12/860,721

(22) Filed: Aug. 20, 2010

(65) Prior Publication Data

US 2012/0045363 A1    Feb. 23, 2012

(51) Int. Cl.
*G01N 21/00* (2006.01)
*A61N 5/00* (2006.01)

(52) U.S. Cl.
USPC ............. 250/492.1; 250/453.11; 250/454.11; 250/494.1; 250/504 R; 607/88; 607/94

(58) Field of Classification Search
USPC ................. 250/453.11, 454.11, 492.1, 494.1, 250/504 R; 422/1, 22, 24, 186.3; 607/88, 94
See application file for complete search history.

(56) References Cited

U.S. PATENT DOCUMENTS

| | | | |
|---|---|---|---|
| 7,875,869 B1 * | 1/2011 | Shadan ................... | 250/504 R |
| 8,241,565 B1 * | 8/2012 | Abdul ..................... | 422/24 |
| 2008/0310996 A1 * | 12/2008 | Kim et al. ............... | 422/24 |
| 2010/0193709 A1 * | 8/2010 | Dalton .................... | 250/504 R |

FOREIGN PATENT DOCUMENTS

JP        59003861 A   *   1/1984

OTHER PUBLICATIONS

English translation of the abstract of JP 59003861 A.*

* cited by examiner

*Primary Examiner* — Monzer Chorbaji
(74) *Attorney, Agent, or Firm* — Larson & Larson PA; Frank Liebenow

(57) ABSTRACT

A portable sterilization device using direct UV-C radiation to sterilize the bottom of footwear from known, multiple sources of contamination including bacteria and viruses. This portable device will offer a safe sterilization method for the general public, both in-home and in commercial use.

9 Claims, 6 Drawing Sheets

PORTABLE STERILIZATION DEVICE FOR FOOTWEAR UTILIZING GERMICIDAL UV-C RADIATION

BACKGROUND

The greatest source of multiple contamination agents introduced to interiors of homes, hospitals, schools, and offices is carried on contaminated bottom of footwear. A recent study by the University of Arizona (2008), confirmed this finding by testing of the bottom of the footwear picked up 420,000 units of bacteria in just two weeks. Of that bacterium, 27% were the deadly E. coli virus. The bacterium, K. pneumonia was also found which can cause pneumonia and sepsis. Also identified was S. ficaria, which can lead to infection of the respiratory tract.

It was found out that a square inch of a typical carpet at home can contain as much as 100,000 of various bacteria and over 16,000 of various bacteria on every square inch of a bathroom floor. The interesting part of this research is that a toilet seat has only 50 bacteria. This confirms that the source of contamination that is being introduced to a typical home is done by contaminated footwear.

Using steam cleaners to kill the bacteria was found ineffective in killing germs and bacteria in Home and public places. Although at the source steam can be 100 degrees C. however by the time this steam gets in contact with the carpets or the floor the temperature drops drastically and as such does not kill the bacteria and the viruses. Chemical products that may be used by spraying or spreading on floors or carpets create potential hazards to health and safety and exacerbate allergies.

In particular, with the probability of a pandemic caused by certain viruses, a portable ultraviolet sterilizing device will be essential in eradicating these viruses.

The best known source of sterilization is UV-C radiation. However this source of radiation used without protective eyewear and shielding the skin from the UV-C rays will create safety hazards. A sterilization device to be used by the public must be designed in a way to completely protect the people from being exposed to UV-C radiation.

UV-C radiation is a unique and rapid method of surface disinfection, utilizing germicidal ultraviolet lamps that produce short wave radiation that is lethal to bacteria, virus, pathogens and other microorganisms.

SUMMARY OF THE DISCLOSURE

The invention generally relates to using UV-C radiation to sterilize the bottom of footwear which may include shoes, athletic shoes, socks, and sandals utilizing a safe and portable device. The invention more particularly relates to a portable device that can be used both in the home and in public places such as hospitals, schools, food preparation areas, office buildings, and other public buildings. This device will be activated by a person stepping on the glass platform. Once activated, the device will turn on a UV-C bulbs which will sterilize the bottom of footwear using UV-C radiation. The bottom of footwear will be exposed for a time specified by and controlled by an electronic timer.

BRIEF DESCRIPTION OF THE DRAWINGS

The drawings attached to this patent application represent the design of a portable sterilization device utilizing UV-C radiation for use by untrained individuals and without the need of any protective gear/eyewear.

GENERAL DESCRIPTION OF THE INVENTION

The invention generally relates to using ultraviolet radiation to sterilize the bottom of footwear which may include shoes, athletic shoes, socks, and sandals utilizing a safe and portable device. The invention more particularly relates to a portable device that can be used both in the home and in public places such as hospitals, schools, office buildings, and other public buildings. This device will be activated by a person stepping on the glass platform and by the presence of footwear in a designated area within the device. Once activated, the device will turn on UV-C bulbs which will sterilize the bottom of footwear using UV-C radiation. The bottom of footwear will be exposed for a time specified by an electronic timer.

Ultraviolet radiation is a unique and rapid method for surface disinfection, utilizing germicidal ultraviolet lamps produce short wave radiation that is lethal to bacteria, virus, pathogens and other microorganisms. However, UV-C radiation is harmful to humans and in particular human eyes. In order to prevent corneal damage, you must wear protective eyewear. Our device circumvents protective eyewear through a protective shield over the stepping platform, which will eliminate any exposure to the UV-C radiation for the person stepping on the device. To add additional protection and safety, we use spring-loaded actuators, calibrated to sense the presence of a person weight, stepping on the device. The spring-loaded actuators will be calibrated to a pre-determined weight in order to activate the micro-switches. This will ensure that no pets, babies, or toddlers will activate the device. In addition, a motion sensing switch needs to be activated by the placement of the footwear completely within a specific area in the device. The device cannot be activated by weight alone and must be activated by a combination of weight and motion sensing switches.

DETAILED DESCRIPTION OF THE DRAWINGS

Figure 1:
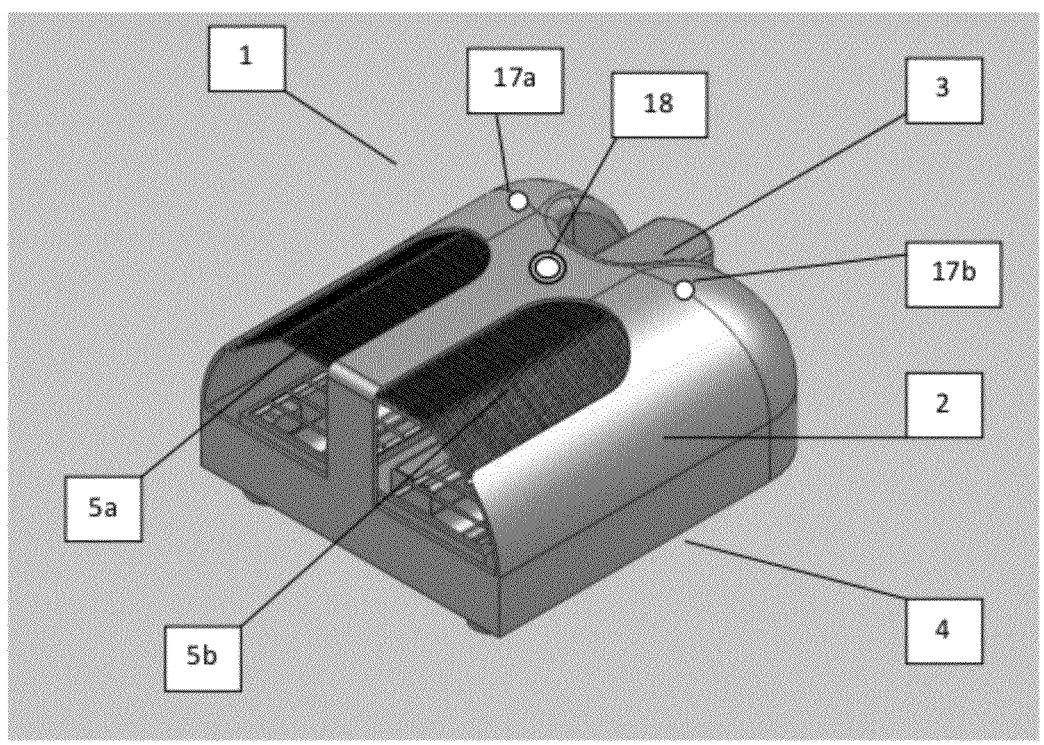
FIG. 1 is a perspective view of the device claimed invention.

In reference to the figures attached:

FIG. 1 is a perspective view of the portable sterilization device 1 (referred hereafter to as the "device"). The device 1 is a free-standing unit. The device 1 is comprised of a base 4, a protective shield 2, a DC battery 3, protective brushes 5a and 5b, LED indicators 17a and 17b, and buzzer 18.

Figure 2:
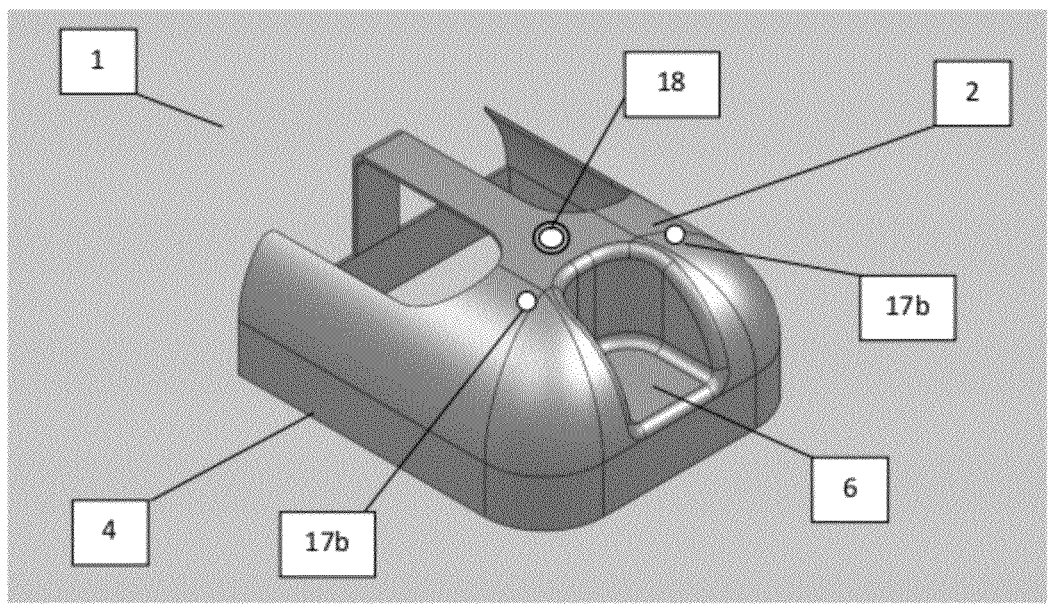
FIG. 2 is a perspective view of the device showing the protective shield used to eliminate exposure to UV-C radiation.

FIG. 2 is a perspective view of the device 1 showing details of the protective shield 2, the base 4, and the battery base 6, LED indicators 17a and 17b, and buzzer 18.

Figure 3:
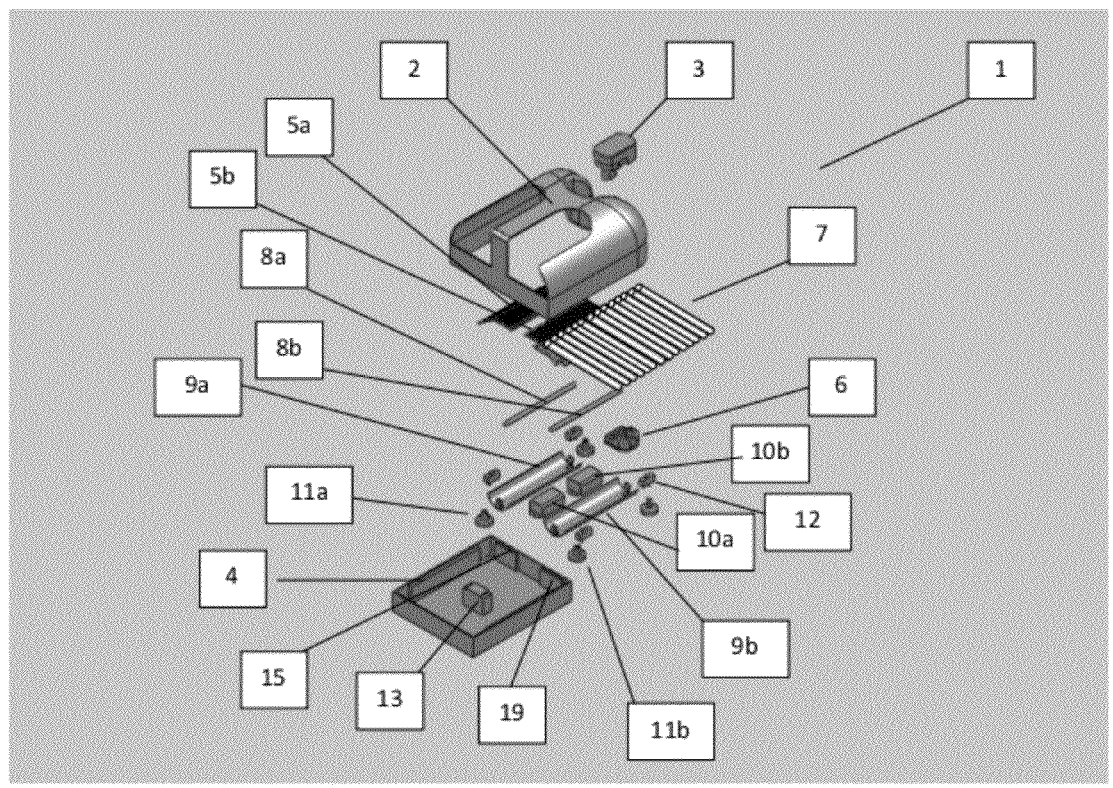
FIG. 3 is an exploded view showing details of all internal components incorporated in the device.

FIG. 3 is an exploded view of the device 1 showing details of all the components comprising device 1. The details of these components are the protective shield 2, the DC battery 3, the base 4, the protective brushes 5, battery base 6, the glass platform 7, UV-C bulbs 8a and 8b, parabolic reflectors 9a and 9b, UV-C ballasts 10a and 10b, spring loaded actuators 11a and 11b, one out of four micro-switches 12, motion sensing switch 13, electronic/electric control box 15, and DC/AC power inverter 19.

Figure 4:
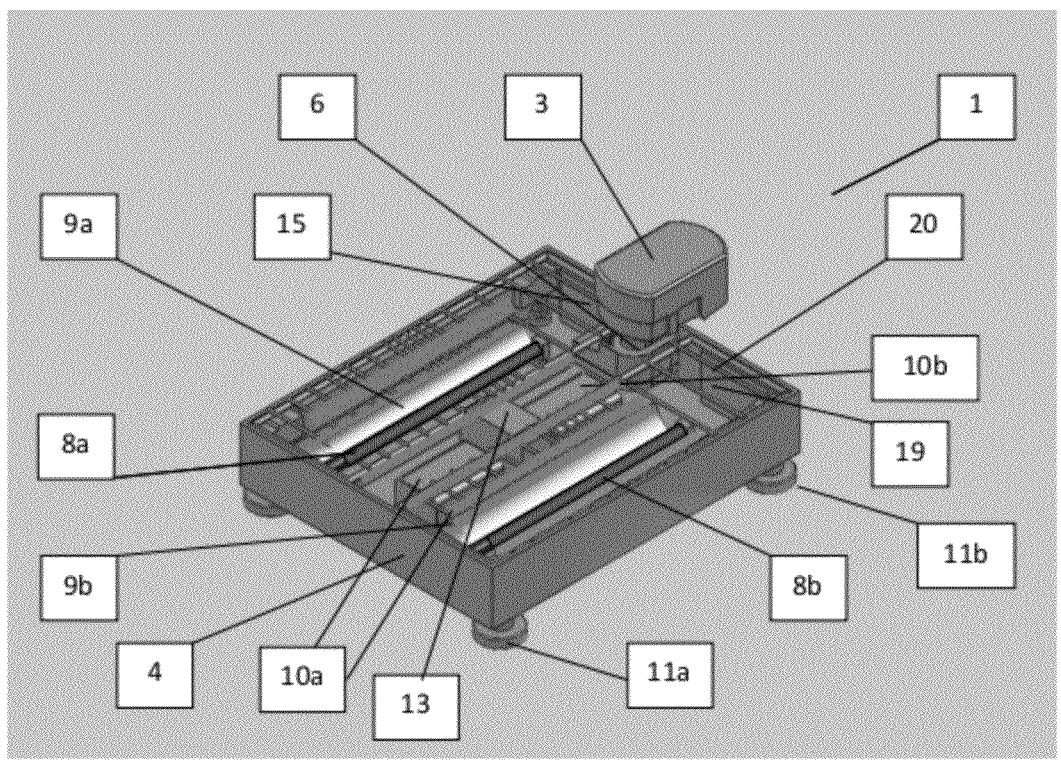
FIG. 4 is a perspective view of the device base showing some of the components incorporated in the base of the device.

FIG. 4 is a perspective view of the device 1 with the protective shield removed and showing DC battery 3, battery base 6, UV-C bulb assembly 8a and 8b, parabolic reflectors 9, ballasts 10a and 10b, spring-loaded actuators 11a and 11b, electronic/electric control box 15, DC/AC power inverter 19, external AC connections 20 bypasses the DC battery 3 and the DC/AC converter 19 supplying direct power to the electronic/electric control box 15.

Figure 5:
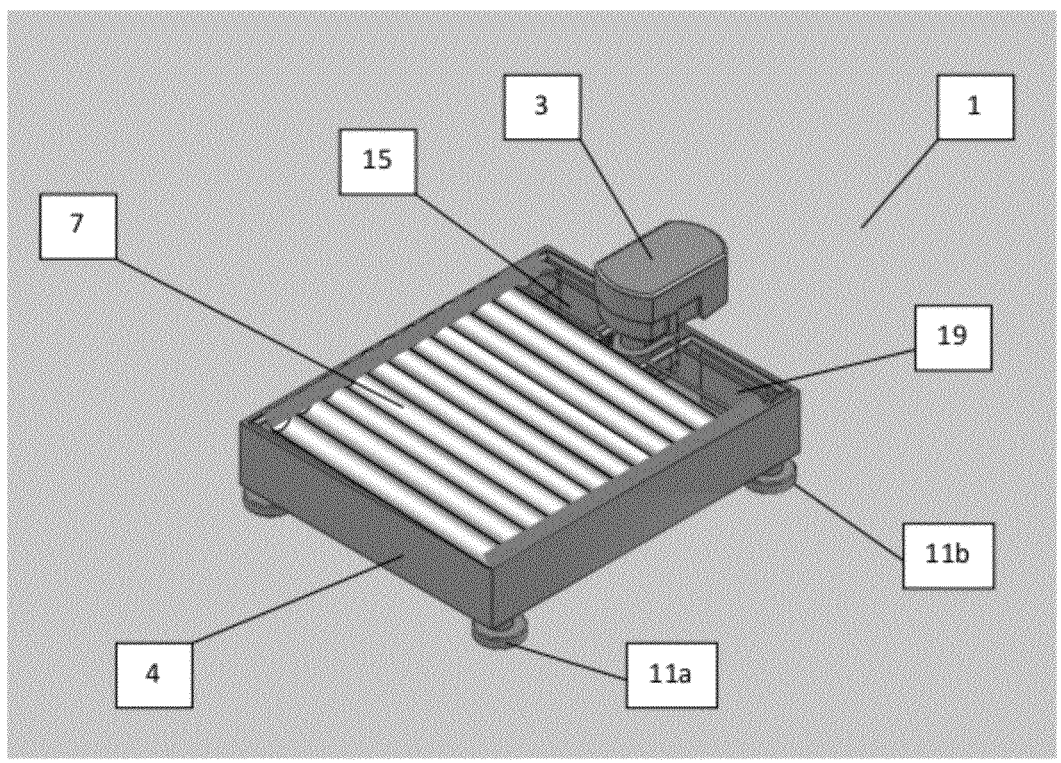
FIG. 5 is a prospective view of the base of the device showing the glass platform.

FIG. 5 is a prospective view of device 1 with the protective shield removed and showing DC battery 3, base 4, glass platform 7, spring-loaded actuators 11a and 11b, electronic/electrical control box 15, and DC/AC power inverter 19.

Figure 6:
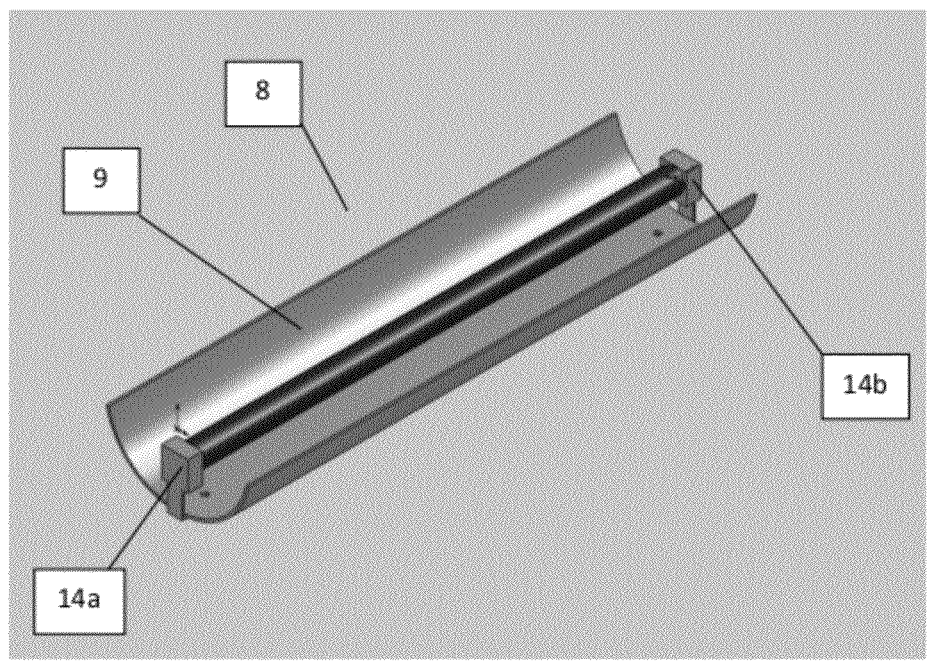
FIG. 6 is a prospective view of the UV-C bulb assembly which includes the specially designed parabolic reflector.

FIG. 6 is a prospective view of the UV-C bulb assembly comprised of UV-C bulb 8, parabolic reflector 9, and two UV-C sockets 14a and 14b.

The invention claimed is:

1. A portable sterilization device utilizing direct UV-C radiation for sterilizing the bottom of footwear from known multiple sources of contamination including bacteria and viruses, molds, dust mite, and fleas, the portable sterilization device comprising:
   a low-profile base having a glass platform which allows the UV-C radiation to radiate through it;
   a UV-C bulb assembly which includes a parabolic reflector within the low-profile base that directs the UV-C radiation to the bottom of the footwear;
   a protective shield over the glass platform for shielding from exposure to the UV-C radiation, the protective shield having a set of protective brushes that allow the person to step on to the glass platform and that simultaneously close around the person's ankle; and further comprising spring-loaded actuators, calibrated to sense the presence of a person's weight stepping on the glass platform, activating the UV-C bulb assembly responsive the presence of the person's weight stepping on the glass platform, wherein the spring-loaded actuators comprise micro-switching devices
   whereas the portable sterilization device is activated by a person stepping upon the glass platform, thereby exposing the bottom of the footwear to the UV-C radiation, thereby rendering bacteria and viruses harmless.

2. The portable sterilization device as in claim 1, wherein the UV-C bulb assembly is powered by a rechargeable battery or, directly by AC power.

3. The portable sterilization device as in claim 2, further comprising LED indicators that are illuminated if the rechargeable battery requires charging.

4. The portable sterilization device as in claim 1, wherein the UV-C bulb assembly is powered by a DC/AC power inverter.

5. The portable sterilization device as in claim 1, wherein further comprising a motion sensing switch that senses the presence of a person's footwear inside the portable sterilization device, thereby activating the UV-C bulb assembly responsive the presence of the person's footwear inside the device.

6. The portable sterilization device as in claim 5, wherein the motion sensing switch further comprises a built-in timer, the timer determines the duration of the UV-C exposure.

7. The portable sterilization device as in claim 6, wherein the built-in timer activates an audible and/or visual indicator when the duration of the UV-C exposure is complete.

8. The portable sterilization device as in claim 1, wherein the parabolic reflector reflects, concentrates, and directs the UV-C radiation upwards towards the bottom of the footwear.

9. The portable sterilization device as in claim 1, wherein the low profile base comprises of a glass platform made in a way to bear weight of a person standing on it but does not the block UV-C radiation.

* * * * *